United States Patent [19]
Kantrowitz et al.

[11] 4,092,742
[45] June 6, 1978

[54] DYNAMIC PROSTHETIC MYOCARDIUM

[75] Inventors: Adrian Kantrowitz, Pontiac; Paul S. Freed, Oak Park, both of Mich.

[73] Assignee: Sinai Hospital of Detroit, Detroit, Mich.

[21] Appl. No.: 733,677

[22] Filed: Oct. 18, 1976

[51] Int. Cl.² ............................................. A61F 1/24
[52] U.S. Cl. ................................... 3/1.7; 128/334 R
[58] Field of Search .......... 3/1.7, 1; 128/1 D, DIG. 3, 128/334 R

[56] References Cited
U.S. PATENT DOCUMENTS

| 3,513,486 | 5/1970 | Bennetot et al. | 3/1.7 |
| 3,874,388 | 4/1975 | King et al. | 128/334 R |

OTHER PUBLICATIONS

"Studies with an Active Prosthetic Myocardium" by O. Hamada et al., Transactions American Society for Artificial Internal Organs, vol. XXI, 1975, pp. 374–379.
"An Experimental Prosthetic Myocardium" by P. Schupbach et al., Transactions Amer. Society for Artificial Internal Organs, vol. XV, 1969, pp. 434–439.

*Primary Examiner*—Ronald L. Frinks
*Attorney, Agent, or Firm*—Cullen, Settle, Sloman & Cantor

[57] ABSTRACT

A prosthetic myocardium is disclosed for replacing necrotic or scarred myocardial tissue to positively simulate both myocardial contraction and expansion during systole and diastole. The prosthetic device includes several circumferentially arranged tilting arms which are sutured to the periphery of an opening in the heart formed by a medical excision. The tilting arms are pivotally supported and functionally interconnected with an axially reciprocal drive rod which effects synchronized inward and outward pivoting of the tilting arms to simulate the myocardial functions during heartbeat.

9 Claims, 3 Drawing Figures

DYNAMIC PROSTHETIC MYOCARDIUM

BACKGROUND OF THE INVENTION

This invention was made in the course of research under a grant from the United States Department of Health, Education, and Welfare.

FIELD OF THE INVENTION

This invention relates generally to a prosthetic device adapted to replace myocardial tissue, and more particularly to such a device which is capable of effecting not only a simulated myocardial contraction, but also a simulated myocardial expansion.

THE PRIOR ART

Various investigations have been conducted and reported in recent years relating to the methods for repairing or assisting the failing heart, particularly with respect to the excision of lage infarcted myocardial regions.

Some early investigations were reported in Surgery, 61: 51, 1967 in an article by R. O. Heimbecker entitled "Surgery for Massive Myocardial Infarction". In most of the early studies, infarcted areas and aneurysms were excised with direct suture techniques for repair of the ventricle, without the implantation of a prosthesis. If an infarcted area was not too large, good results were obtained on many ocassions; however, the volume of the left ventricle was decreased even with relatively small excisions. In patients with large infarctions or aneurysms, resection of the left ventricular myocardium impairs the contractility of the remaining muscle and diminishes its ability to eject an adequate blood supply into the systemic and coronary circulation. This latter condition may lead to failure when the heart is resuscitated.

Later studies have been directed at developing mechanical approaches to augment ventricular functions with experimental prostheses, as reported in an article in the *Trans American Society of Artificial Internal Organs,* Volume XV,1969 by Schupbach. According to this publication, a portion of the excised myocardium was replaced with either an ellipsoidal or a flat device which incorporated a pumping chamber with a pumping action synchronized to the heart beat to increase left ventricular pressure during systole. Improved hemodynamics of the circulation was achieved by this device, but to perform effectively the device had to be implanted in the apex of the heart, which is a relatively infrequent site of myocardial infarction. Because of this limitation, emphasis was placed on another prosthesis under consideration at that time, the dynamic aortic patch which has since been developed.

One of the latest versions of a prosthetic myocardium is reported in *Trans American Society of Artificial Internal Organs,* Volume XXV, 1975 in an article by Hamada, entitled "Studies with an Active Prosthetic Myocardium". The prosthetic device reported in this publication included several sutures attached to the rim of a circular patch covering the opening in the heart. During systole the sutures were tensioned to create a contraction, and during diastole the sutures were released to enable expansion of the ventricle. This particular publication extensively reported test cases showing that prosthetic myocardial devices provide quite promising results. However, it has been found that the prosthesis described in this publication compromises left ventricular filling under certain conditions because there is no positive means to simulate myocardial expansion during diastole.

Accordingly, prior to the presently disclosed invention, the prior art had not provided a permanently implantable prosthetic myocardium capable of mimmicking or simulating the overall myocardial functions.

Each of the previously discussed publications are incorporated herein by reference. The publications by Schupbach and Hamada are particularly noted for their disclosure of test cases using a prosthetic myocardium.

SUMMARY OF THE INVENTION

The present invention overcomes the disadvantages and shortcomings in the prior art by providing a dynamic prosthetic myocardium which is implantable to replace the function of heart tissue which has either been impaired by an extensive infarct or scar or removed by surgical excision.

The disclosed prosthetic myocardial device includes a plurality of circumferentially arranged arms which are supported at one of their ends for pivotal movement. The other ends of the arms are capable of being sutured to the heart around the periphery of an opening formed by the excision of impaired myocardial tissue. Power means is provided for effecting synchronous pivotal movement of the arms to simulate myocardial contraction and relaxation of the heart during systole and diastole. The power means includes a pneumatic cylinder, a piston which is reciprocable within the cylinder, and a piston rod extending out of the cylinder coaxially of the circumferentially arranged pivotal arms. Tilting means functionally interconnect the piston rod and each of the pivotal arms for effecting synchronous reciprocal pivotal movement of the arms in response to the reciprocal axial movement of the piston rod.

In a preferred embodiment, the tilting means includes a disc-shaped cam on the piston rod and a cam surface on each of the pivotal arms. Also, in the most preferred embodiment each of the pivotal arms includes a major leg which is essentially perpendicular to the immediately adjacent myocardial tissue to which it will be sutured. The other end of the leg extends outwardly away from the interior of the heart. A secondary leg at the extending end of the primary leg projects radially inward with respect to the opening of the heart and forms an included angle with the primary leg of less than 90°. A third leg extends radially inward from an intermediate portion of the primary leg and, in corporation with the secondary leg, forms an essentially V-shaped camfollower surface within which the disc-shaped cam nests.

The utility of the disclosed prosthetic myocardial device has been proven in tests undertaken with mongrel dogs in a manner similar to those reported in the publications by Schupback and Hamada. In the tests using the prosthesis of this invention, left ventricular systolic and end-diastolic pressures and cardiac output all improved while the device was active.

Accordingly, the present invention provides an implantable prosthetic device which can effectively replace relatively large infarcted regions of the myocardium and simulate the functions of the excised tissue. The numerous advantages and meritorious features of the inventon will be more fully appreciated from the following detailed description and the appended claims.

DETAILED DESCRIPTION OF THE PREFERRED EMBODIMENT

Referring more particularly to the drawings, where a prosthetic myocardial device 10 according to the present invention is sutured to the periphery of an opening in the heat 12 formed by excising necrotic or diseased myocardial tissue. As illustrated, a circular knitted Dacron velour patch 14 is sutured over the opening of the heart to prevent the loss of blood. The patch 14 is coated on its inner cloth side with a medical grade adhesive to block the seepage of blood through the material. The outer 1½ centimeter rim of the material is preferably left untreated to facilitate the suturing of the patch to the myocardium. In attaching the patch to the myocardial tissue, the patch is placed over the opening with the velour facing the blood interface and then sutured to the endocardial surface of the myocardium with individual matress sutures, reinforced with Teflon felt. An annular reinforcing strip 16 of similar material may be sutured to the outer surface of the myocardium to relieve the stress of the sutures on the tissue.

Figure 1:
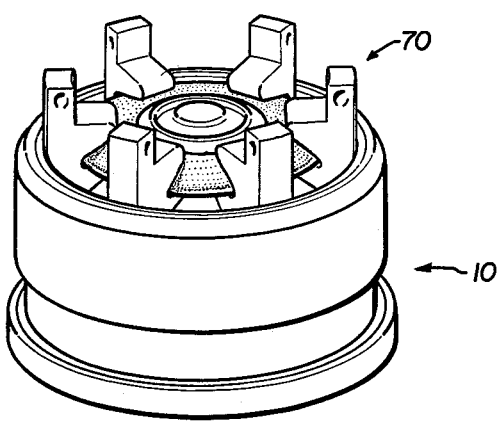
FIG. 1 is a perspective view of the prosthetic myocardial device.
Figure 2:
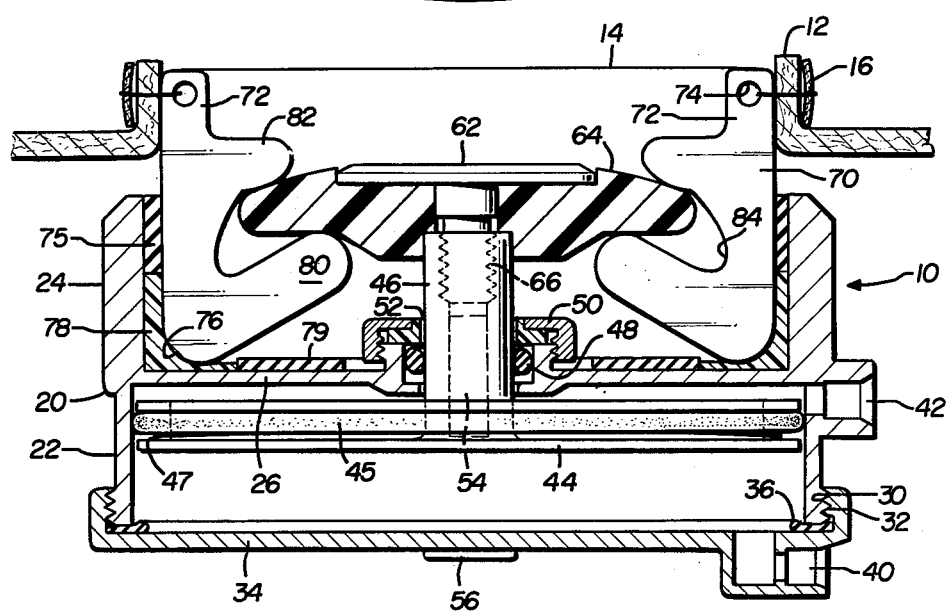
FIG. 2 is a cross sectional view of the prosthetic myocardial device, illustrating the component parts in a position representing end-diastolic movement.
Figure 3:
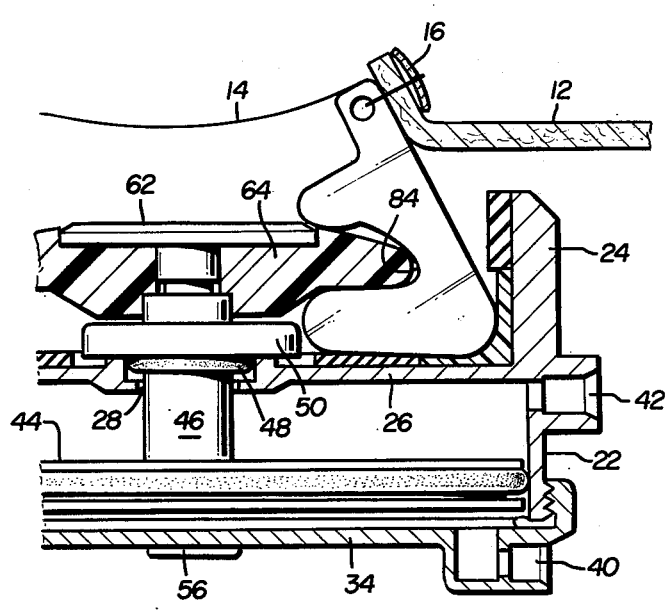
FIG. 3 is a cross sectional view similar to FIG. 2, illustrating the component parts of the prosthetic device in an end-systolic position.

Referring now to FIGS. 2 and 3, the prosthetic myocardial device is shown in greater detail as including a cylindrical housing 20 having a lower cylindrical wall 22 and an upper cylindrical wall 24 separated by an intermediate inward radial wall 26 having a central opening 28. The bottom portion of lower cylindrical wall 22 is threaded, as shown by reference numeral 30, to receive threads 32 on an end cap 34. An optional gasket 36 of silicone rubber material is positioned between the outer annular edge of the end cap 34 and the bottom end of lower cylindrical wall 22 to provide a seal. By comparing FIG. 1 with FIGS. 2 and 3, it will be readily appreciated that the end cap 34 faces outwardly away from the heart when the prosthesis is implanted in a patient.

As shown, the lower cylindrical wall 22, the end cap 34, and the intermediate radial wall 26 collectively define a chamber having ports 40 and 42 to receive presurized air from a suitable source (not shown) for reciprocating a piston 44 within the chamber. As will become more fully apparent in the following portions of this disclosure, air under pressure is supplied to and vented from both ports 40 and 42 in synchronism with the heart beat from an air source which is preferably compact and mobile to permit both the mobility of the patient and the permanent implantation of the prosthesis. In order to synchronize the operation of the piston and cylinder with the heart beat, the pressure source may be actuated in response to the R-wave of an electrocardiogram, or its equivalence.

The outer peripheral edge of the piston 44 includes a groove 47 within which an O-ring 45 is nested for sealing purposes. Likewise, an O-ring 48 is nested within a circumferential groove formed by the inward radial portion of intermediate wall 26 and a threaded cap 50. As shown, the O-ring 48 bears against the outer cylindrical surface of a piston rod 46 which projects upwardly from piston 44 through a central opening 28. To reduce wear and to center the piston rod, an annular ring 52 of ultra-high molecular weight polyethylene is held in position by the threaded cap 50.

Optionally, the piston rod 46 is tubular in configuration to receive a cylindrical magnet 54 which cooperates with a Hall-Effect sensor 56 to monitor the position of the piston during its reciprocal movement. As is known by those skilled in the art, a Hall-Effect sensor produces a current which is proportional to the strength of a magnetic field. Therefore, when the piston is in the position shown in FIG. 2 at an end-diastolic stroke, a relatively small electrical impulse generated by the Hall-Effect sensor can be read by suitable monitoring equipment (not shown). Correspondingly, when the piston is at the end-systolic stroke shown in FIG. 3, a stronger electrical impulse is generated which is likewise monitored.

The upper internal end of the piston rod 46 has threads 60 to receive the threaded shaft of a cap 62 which secures a disc-shaped, polyethylene cam 64 to the piston rod.

The cam 64 extends radially outward to nest within a cam follower notch 84 on each of a plurality of circumferentially arranged pivotal arms 70. The precise number of pivotal arms may be varied to accomodate the size of the myocardial opening and to distribute the forces generated by the prosthetic device during operation. In the preferred embodiment, six pivotal arms 70 are provided around the periphery of the myocardial opening shown in FIG. 1.

Each arm 70 includes a primary or major upstanding leg 72 having an opening 74 at its upper end to receive a suture for interconnection with the myocardial wall. An intermediate portion of the leg 72 contacts a compressible silicone rubber pad 75 secured to the interior of upper cylindrical wall 24, to cushion the pivotal or rocking motion of the arm. The lower end 76 of leg 72 is pivotally supported by an annular L-shaped support pad 78 comprised of a suitable material, such as ultra-high molecular weight polyethylene. An optional annular pad 79 of silicone rubber material is secured to a portion of intermediate wall 26 to cushion the displacement of the rocking arms in the position shown in FIG. 3.

Each pivotal arm 70 also includes a secondary leg 80 extending radially inward from the bottom of leg 72 and forming an included angle, as shown, of approximately 50°. As will be appreciated, this angle may be varied, but must be somewhat less than 90° to enable the pivotal or rocking motion of arm 72.

A third leg 82 projects radially inward from an intermediate portion of the major upstanding leg 72 and forms a somewhat V-shaped cam surface 84 in combination with the secondary leg 80.

In operation, the pivotal arms 70 will be sutured appropriately at opening 74 to the periphery of an opening in the myocardium. With the prosthetic myocardial device positioned as shown in FIG. 2, the heart will be at the end of a diastolic expansion just prior to the initiation of a systolic contraction. For the disclosed prosthetic device to simulate the following myocardial function, air or a similar conventional fluid is supplied through port 42 to cause piston 44 and piston rod 46 to move toward end cap 34. During this portion of the piston stroke, the disc-shaped cam 64 exerts a pressure upon the secondary legs 80 to cause the tilting arms 70 to pivot upon end surface 76 as supported by pad 78. During this phase of operation, the upper ends of the tilting arms 70 are displaced radially inwardly to simulate systolic contraction., as shown in FIG. 3. Also during this phase of operation, air between the bottom portion of piston 44 and cap 34 is vented through port 40.

With the prosthetic myocardial device in the position shown in FIG. 3, the heart will be at the beginning of a diastolic expansion. So that the prosthetic device may positively simulate this phase of heart function, the piston 44 is forced upwardly by the introduction of air under pressure from port 40. Accordingly, the upper surface of disk-shaped cam 64 exerts pressure upon the lower surface of inward radial legs 82 to cause tilting arms 70 to pivot outwardly upon support surfaces 76, again achieving the position shown in FIG. 2. As will be apparent, during this phase of operation, air between piston 44 and intermediate wall 26 is vented through port 42.

It is to be understood from the scope of the following claims that the foregoing disclosure is exemplary in nature rather than limiting. For example, the other mechanical configurations may be used.

Accordingly, having fully and completely disclosed our invention, we now claim:

1. A prosthetic myocardial device for replacing excised necrotic or scarred myocardial tissue to simulate contraction and relaxation during systole and diastole, comprising:
   a plurality of essentially circumferentially arranged arms, with each of the arms being supported at one of its ends for pivotal movement and the other end of each arm being adapted for suture to the heart around the periphery of an opening formed by excising myocardial tissue; power means for effecting synchronous pivotal movement of said plurality of arms to simulate contraction and relaxation of the heart, including an hydraulic cylinder, a piston reciprocable within the cylinder, and a piston rod extending out of the cylinder and being essentially coaxial of the circumferentially arranged pivotal arms; and tilting means functionally interconnecting the piston rod and each of the pivotal arms for effecting reciprocal pivotal movement of the arms in response to the reciprocal axial movement of the piston rod.

2. The prosthetic myocardial device as defined in claim 1 characterized by said tilting means including (a) a disc-shaped cam on the piston rod and (b) a cam surface on each of the pivotal arms.

3. The prosthetic myocardial device as defined in claim 2, characterized by each said cam surface being formed by a pair of inward radial arms on each of the pivoting arms, forming an essentially V-shaped cam surface within which the disc-shaped cam is received.

4. A dynamic prosthetic myocardium for replacing surgically excised myocardial tissue, including:
   a housing comprised of an essentially cylindrical side wall, a closure on one end of the cylindrical side wall, and an intermediate wall extending radially inward from the sidewall and having a central opening; the closure and the intermediate wall forming a chamber within which an axially reciprocal piston is housed; a piston rod extending from the piston through the central opening in the intermediate wall and having an essentially disc-shaped cam carried on its distal end; a plurality of radially arranged, circumferentially spaced cam follower means nested within the housing between the open end of the housing and the intermediate wall and interengaging the disc-shaped cam for translating the axial motion of the piston rod into essentially radial motion to simulate myocardial contraction and relaxation during systole and diastole; each of the cam follower means being interconnectable to myocardial tissue; and a port at each axial end of the housing chamber to accomodate the flow of fluid for effecting axial movement of the piston, piston rod and disc-shaped cam.

5. The dynamic prosthetic myocardium defined in claim 4, wherein each of said cam foller means includes an arm which is pivotally supported at one of its ends and with the other end of the arm extending beyond the open end of the cylindrical wall for suture to the heart, said disc-shaped cam effecting pivotal movement of said arms to achieve said simulated myocardial contraction and relaxation.

6. A prosthetic myocardial device, comprising:
   a plurality of essentially circumferentially arranged tilting arms adapted to be sutured to the periphery of an opening of the heart formed by the excision of myocardial tissue; each of the arms having (a) a primary leg with one end of the primary leg adapted to be sutured to the surrounding myocardial tissue, (b) a secondary leg at the other end of the primary leg forming an included angle with the primary leg of less than 90 degrees, and (c) a tertiary leg extending radially inward from an intermediate portion of the primary leg, with the secondary and tertiary legs forming opposed cam-follower surfaces;
   an essentially tubular housing within which the tilting arms are nested and means for pivotally supporting said other ends of the primary legs; a disc-shaped cam means received between the secondary and tertiary legs on each of said tilting arms for (a) reciprocating axially with respect to each of the circumferentially arranged tilting arms, (b) alternately engaging the second and tertiary legs during reciprocal movement thereof to pivot each of the primary legs about its said other end, and (c) effecting an essentially radial inward and outward movement of said one end of the primary legs to simulate myocardial contraction and expansion during systole and diastole.

7. The prosthetic myocardial device defined in claim 6, further including displacement means for effecting the axial reciprocation of said disc-shaped cam.

8. The prosthetic myocardial device defined in claim 6, characterized by said means for pivotally supporting the tilting arms including an annular elbow support surface on the interior of the tubular housing.

9. The prosthetic myocardial device defined in claim 7, wherein said displacement means includes a pneumatic cylinder within which a piston is axially reciprocated in response to the fluid under pressure, and a piston rod interconnecting the piston and said disc-shaped cam.

* * * * *